United States Patent [19]
Macioszek et al.

[11] Patent Number: 5,968,739
[45] Date of Patent: Oct. 19, 1999

[54] **NUCLEIC ACID PRIMERS AND PROBES FOR DETECTING *LEGIONELLA PNEUMOPHILA***

[75] Inventors: Jerzy A. Macioszek, Lindenhurst, Ill.; Bor-Chian Lin, San Diego, Calif.; Arthur E. Martinez, Gurnee, Ill.

[73] Assignee: Abbott Laboratories, Abbott Park, Ill.

[21] Appl. No.: 08/763,030

[22] Filed: Dec. 10, 1996

[51] Int. Cl.$^6$ .................................................. C12Q 1/68
[52] U.S. Cl. .......................... 435/6; 435/91.1; 435/91.2; 536/23.1; 536/24.3; 536/24.32; 536/24.33
[58] Field of Search ............... 435/6, 91.1, 91.2; 536/24.32, 24.3, 24.33, 23.1

[56] References Cited

U.S. PATENT DOCUMENTS 5,298,392  3/1994  Atlas et al. ............................. 435/600
5,491,225  2/1996  Picone et al. ......................... 536/24.32

FOREIGN PATENT DOCUMENTS 0438115  7/1991  European Pat. Off. .
9211273  7/1992  WIPO .

OTHER PUBLICATIONS

Engleberg, N.C., et al., "DNA Sequence of mip, a *Legionella pneumophila* Gene Associated with Macrophage Infectivity", *Infection and Immunity*, 57(4):1263–1270 (1989).
Perkin Elmer kit insert, "EnviroAmp™", *Legionella Kits*, 1–40 (1993).

*Primary Examiner*—Nancy Degen
*Assistant Examiner*—Irem Yucel
*Attorney, Agent, or Firm*—Paul D. Yasger

[57] ABSTRACT

Nucleic acid sequences that are useful for detecting *Legionella pneumophila* are herein provided. These sequences can be used in hybridization assays or amplification based assays designed to detect the presence of *Legionella pneumophila* in a test sample. Additionally, the sequences can be provided as part of a kit.

5 Claims, No Drawings

5,968,739

NUCLEIC ACID PRIMERS AND PROBES FOR DETECTING *LEGIONELLA PNEUMOPHILA*

FIELD OF THE INVENTION

The present invention relates to *Legionella pneumophila* and in particular, it relates to oligonucleotides and methods for detecting *Legionella pneumophila* in a test sample.

BACKGROUND OF THE INVENTION

A genus of bacteria known as Legionella contains approximately 30 different species. One species, *Legionella pneumophila* (*L. pneumophila*) is the causative agent for approximately 90% of all cases of an affliction known as Legionnaires' disease. Legionnaires' disease makes up 5–8% of atypical pneumonia cases and up to 20% of the Legionnaires' related atypical pneumonia cases are lethal and there are several serogroups within *L. pneumophila* associated with Legionnaires disease.

Currently, diagnosing Legionnaires disease typically requires detecting *L. pneumophila* in an appropriate sample which can be accomplished by growing *L. pneumophila* in culture, fluorescent antibody staining, or urinary antigen testing. Unfortunately, these methods can be time consuming and are not always sensitive. Additionally, not all of these techniques are capable of detecting all *L. pneumophila* serogroups and therefore may yield false negative test results in assays designed to detect *L. pneumophila* in a test sample. Accordingly, there is a need for methods and reagents capable of detecting *L. pneumophila* in a test sample that are both sensitive and sufficiently specific to detect disease causing *L. pneumophila* serogroups without detecting other Legionella species.

SUMMARY OF THE INVENTION

The present invention provides oligonucleotides that can be used to sensitively detect disease causing *L. pneumophila* serogroups without detecting other Legionella species. These sequences can be employed as hybridization probes or amplification primers to specifically and sensitively detect *L. pneumophila* serogroups 1–14. The oligonucleotides provided herein are designated SEQ ID NO 2 and its complement SEQ ID NO 3; SEQ ID NO 4 and their respective complements SEQ ID NO 5; SEQ ID NO 6 and SEQ ID NO 7. Those skilled in the art will recognize that homologs of these sequences and combinations of these sequences can also be employed to detect *L. pneumophila* in a test sample. Preferably, the sequences are employed in amplification reactions and can be provided in kits along with other reagents for performing an amplification reaction.

Methods provided by the present invention include hybridization assays as well as amplification based assays. Thus, according to one method, a method of detecting the presence of *L. pneumophila* in a test sample comprises the steps of (a) contacting the test sample with one or more of the sequences listed above, or their homologs; and (b) detecting hybridization between the above sequences and a *L. pneumophila* target sequence in the test sample.

According to another embodiment, a method for detecting the presence of *L. pneumophila* in a test sample comprises the steps of (a) forming a reaction mixture comprising nucleic acid amplification reagents, a test sample containing a *L. pneumophila* target sequence, and at least one primer and one probe oligonucleotide selected from the group consisting of SEQ ID NOs. 2 and 7, SEQ ID NOs. 3 and 4, or SEQ ID NOs. 2, 3 and 4; (b) subjecting the mixture to hybridization conditions to generate at least one nucleic acid sequence complementary to the target sequence; (c) hybridizing the probe to the nucleic acid sequence complementary to the target sequence, so as to form a complex comprising the probe and the complementary nucleic acid sequence; and (d) detecting the so-formed complex as an indication of the presence of *L. pneumophila* in the sample.

According to another embodiment, the invention provides kits which comprise a set of oligonucleotide primers and probes, selected from the SEQ ID NOs. listed above, and amplification reagents.

DETAILED DESCRIPTION OF THE INVENTION

As previously mentioned, the present invention provides oligonucleotides, methods for using these oligonucleotides and kits containing these oligonucleotides, all of which can be employed to specifically detect *L. pneumophila*. The oligonucleotides provided are designated herein as SEQ ID NOs. 2, 3, 4, 5, 6 and 7 and homologs thereof. These oligonucleotides hybridize with a *L. pneumophila* target sequence designated herein as SEQ ID NO. 1 or its complementary sequence.

With respect to the sequences herein provided, the term "homologs" means those oligonucleotides sharing 85% homology with SEQ ID NOs. 2–7 and more preferably those oligonucleotides that share 95% homology with SEQ ID NOs. 2–7. Thus, oligonucleotides that share 85% homology with the sequences provided herein and specifically hybridize with the *L. pneumophila* target sequence are intended to be within the scope of the present invention. For example, extensions of the present oligonucleotides, sequences that are shorter than the present oligonucleotides but contain a subset of the present oligonucleotides, and those oligonucleotides that deviate from the present oligonucleotides by minor base substitutions (e.g. 1 or 2 nucleotides) are contemplated as within the scope of the present invention.

Those skilled in the art will recognize various modifications that can be made to the oligonucleotides designated SEQ ID NO 3, SEQ ID NO 4, SEQ ID NO 5, SEQ ID NO 6, SEQ ID NO 7, and SEQ ID NO 8 without departing from their ability to specifically detect *L. pneumophila* and share 85% homology with these sequences. For example, 3' or 5' extensions of the present oligonucleotides with bases that are complementary to succeeding or preceding bases in the *L. pneumophila*target sequence are considered to be homologs of the present oligonucleotides when they share 85% homology with the present oligonucleotides and specifically detect *L. pneumophila*. Additionally, 3' or 5' extensions of present oligonucleotides with bases that are not complementary to succeeding or preceding bases in either of the *L. pneumophila* target sequences that share 85% homology with the present oligonucleotides and specifically detect *L. pneumophila* are contemplated as within the scope of the present invention. Further, base substitutions can be made to SEQ ID NOs. 2–7 but these modified sequences will nevertheless maintain the ability to specifically hybridize with *L. pneumophila* and share 85% homology with the sequences provided herein. Oligonucleotides that are so-modified, are therefore contemplated as within the scope of the present invention. Moreover, oligonucleotides that contain 85% of the oligonucleotides designated SEQ ID NOs. 2–7 but have bases deleted from the 3' or 5' end, are considered to be within the scope of the term homolog.

The oligonucleotides disclosed herein, as well as their homologs, may comprise deoxyribonucleic acid (DNA), ribonucleic acid (RNA) or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. patent applications Ser. Nos 5,464,746; 5,424,414; and 4,948,882 all of which are herein incorporated by reference.

The term "label" as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

The oligonucleotides provided herein can be employed to detect the presence of L. pneumophila in a test sample by contacting a test sample with at least one of the oligonucleotides provided herein under hybridizing conditions and detecting hybridization between the L. pneumophila target sequence and at least one of the oligonucleotides designated herein as SEQ ID NO 3, SEQ ID NO 4, SEQ ID NO 5, SEQ ID NO 6, SEQ ID NO 7, and SEQ ID NO 8. Several well known methods for detecting hybridization can be employed according to the present invention and may include, for example, the use of gels and stains or detecting a label associated with one or more of the sequences provided herein after performing, for example, a dot blot or amplification reaction.

The term "test sample" as used herein, means anything suspected of containing the L. pneumophila target sequence. The test sample can be derived from any biological source, such as for example, blood, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid, tissues such as heart tissue and the like, or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, purifying nucleic acids, and the like.

A "target sequence" as used herein means a nucleic acid sequence that is detected, amplified, or both amplified and detected. Additionally, while the term target sequence is sometimes referred to as single stranded, those skilled in the art will recognize that the target sequence may actually be double stranded.

"Hybridization" or "hybridizing" conditions are defined generally as conditions which promote annealing between complementary nucleic acid sequences or annealing and extension of one or more nucleic acid sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer, probe, or primer and probe set is well within ordinary skill of one practicing this art.

The oligonucleotides provided herein can be used as amplification primers according to nucleic acid amplification procedures well known in the art. Such reactions include, but are not intended to be limited to, the polymerase chain reaction (PCR) described in U.S. Pat. Nos. 4,683,195 and 4,683,202, the ligase chain reaction (LCR) described in EP-A-320 308, and gap LCR (GLCR) described in U.S. Pat. No. 5,427,930 all of which are herein incorporated by reference.

According to a preferred embodiment, the sequences are employed in the "oligonucleotide hybridization PCR" (variably referred to herein as "OH PCR") amplification reaction as described in U.S. patent application Ser. No. 08/514,704, filed Aug. 14, 1995, that is herein incorporated by reference. Briefly, the reagents employed in the preferred method comprise at least one amplification primer and at least one internal hybridization probe, as well as other reagents for performing an amplification reaction.

The primer sequence is employed to prime extension of a copy of a target sequence (or its complement) and is labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

"Other reagents for performing an amplification reaction" or "nucleic acid amplification reagents" include reagents which are well known and may include, but are not limited to, an enzyme having polymerase activity, enzyme cofactors such as magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

The preferred method generally comprises the steps of (a) forming a reaction mixture comprising nucleic acid amplification reagents, at least one hybridization probe, at least one amplification primer and a test sample suspected of containing a target sequence; (b) subjecting the mixture to hybridization and extension conditions to generate at least one copy of a nucleic acid sequence complementary to the target sequence; (c) hybridizing the probe to the nucleic acid sequence complementary to the target sequence, so as to form a hybrid comprising the probe and the nucleic acid sequence complementary to the target sequence; and (d) detecting the hybrid as an indication of the presence of *L. pneumophila* in the sample. It will be understood that step (b) of the above method can be repeated several times prior to step (c) by thermal cycling the reaction mixture as is well known in the art.

According to the above method, it is preferable to select primers, probes and reaction conditions such that the probe sequence has a lower melt temperature than the primer sequences so that upon placing the reaction mixture under hybridization conditions copies of the target sequence or its complement are produced at temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid for example between about 8 minutes to about 15 minutes, preferably less than 2 minutes. Such a rapid cooling favors copy sequence/probe hybridization rather that primer/copy sequence hybridization and extension.

Upon formation of the copy sequence/probe hybrids, the differential labels (i.e. capture and detection labels) on the copy sequence and probe sequence can be used to separate and detect such hybrids. Preferably, detection is performed according to the protocols used by the commercially available Abbott LCx® instrumentation (Abbott Laboratories; Abbott Park, Ill.).

Thus, keeping the preferred method in mind, the oligonucleotides of the present invention are preferably provided in groups of at least two different sequences (i.e. at least one primer sequence and at least one probe sequence complementary to the extension product of the primer). Hence, SEQ ID NOs. 2 and 7, SEQ ID NOs. 3 and 4, or SEQ ID NOs. 2, 3 and 4, or homologs of these sequences are preferably provided together.

The oligonucleotides of the present invention can be provided as part of a kit useful for detecting *L. pneumophila*. The kits comprise one or more suitable containers containing one or more sequences according to the present invention, an enzyme having polymerase activity, and deoxynucleotide triphosphates. Typically, at least one sequence bears a label, but detection is possible without this.

The following examples are provided to further illustrate the present invention and not intended to limit the invention.

EXAMPLES

The following examples demonstrate *L. pneumophila* detection using the DNA oligomer primers and probes herein provided. These DNA primers and probes are identified as SEQUENCE ID NO. 2, SEQUENCE ID NO. 3 and SEQUENCE ID NO. 4. SEQUENCE ID NOs. 2, 3 and 4 are specific for the MIP gene of *L. pneumophila*. A portion of the MIP sequence is designated as SEQUENCE ID NO. 1. In the following examples, SEQUENCE ID NO. 2 and SEQUENCE ID NO. 3 are used as *L. pneumophila* amplification primers specific for the MIP region. SEQUENCE ID NO. 4 is used as an internal hybridization probe for the MIP amplification product.

Example 1

Preparation of *L. pneumophila* Primers and Probes

Target-specific primers and probes were designed to detect the *L. pneumophila* MIP target sequence by oligonucleotide hybridization PCR. These primers were SEQUENCE ID NO. 2 and SEQUENCE ID NO. 3. Primer sequences were synthesized using standard oligonucleotide synthesis methodology and haptenated with adamantane at their 5' ends using standard cyanoethyl phosphoramidite coupling chemistry as described in U.S. Pat. No. 5,424,414 incorporated herein by reference.

The detection probe was designed to hybridize with the amplified *L. pneumophila* MIP target sequence by oligonucleotide hybridization. This probe is SEQUENCE ID NO 4. The probe sequence was synthesized using standard oligonucleotide synthesis methodology and haptenated with 2 carbazoles at the 5' end using standard cyanoethyl phosphoramidite coupling chemistry as described in U.S. Pat. No. 5,464,746 (herein incorporated by reference), and blocked with phosphate at the 3' end.

Example 2

Sensitivity of *L. pneumophila* Detection

Purified DNA from fifteen samples representing fourteen serotypes of *L. pneumophila* was obtained from Biotech Research Labs (BRL), Rockville, Md. The 14 samples of *L. pneumophila* represented American Type Culture Collection (ATCC) Nos. 33153, 33154, 35251, 33156, 33216, 33215, 33823, 35096, 35289 (subspecies pneumophila), 43283, 43130, 43290, 43736 and 43703 (subspecies pascullei) respectively. Serogroups 3, 4 and 5 were all of the subspecies fraserii. DNA was extracted and purified from the cell cultures at BRL by lysing the cells with detergent and high salt, digesting proteins with Proteinase K, then isolating DNA using phenol/chloroform extraction and ethanol precipitation. RNase digestion was done following DNA extraction and precipitation, with phenol/chloroform extraction and ethanol precipitation repeated after RNase digestion.

Dilutions of the DNA purified from the 14 *L. pneumophila* cell lines were PCR amplified and detected using the primers (SEQ ID NOs. 2 and 3) and detection probe (SEQ ID NO. 4) described in Example 1. Taq polymerase was used at a concentration of 2 units/reaction and the final concentration of nucleotides was 0.2 mM each in a total reaction volume of 0.2 ml. PCR extension was performed using 1OX PCR buffer (Perkin Elmer, Foster City, Calif.) which consists of 100 mM Tris-HCl, pH 8.3, 500 mM KCl, at a final concentration of 1×. The reaction mixtures contained primers at a concentration of 100 nM each, and 5 nM of detection probe, with a final concentration of 1.5 mM $MgCl_2$, 10 µg/ml salmon sperm DNA (Sigma Chemical Co, St. Louis, Mo.) and 5 µg/ml bovine serum albumin (BSA). Testing was done using a sample size of 100 µl, in duplicate, with calf thymus DNA as a negative control assayed in triplicate.

Reaction mixtures were amplified in a Perkin-Elmer 480 Thermal Cycler. The following cycling conditions were used: 95° C. for 2 minutes followed by cycling at 95° C. for 15 seconds/60° C. for 30 seconds/72° C. for 30 seconds for 40 cycles. After the reaction mixtures were thermal cycled, the mixtures were maintained at 72° C. for 2 minutes then raised 20 to 97° C. for 5 minutes. Probe oligo hybridization was accomplished by lowering the temperature to 15° C. in approximately two minutes. Following probe hybridization, samples were either assayed immediately or held at 15° C., for up to 24 hours before being tested.

Reaction products were detected on the Abbott LCx® system (available from Abbott Laboratories, Abbott Park, Ill.) A suspension of anti-carbazole antibody coated microparticles and an anti-adamantane antibody/alkaline phosphatase conjugate (all of which are commercially available from Abbott Laboratories, Abbott Park, Ill.) were used in conjunction with the LCx® to capture and detect the reaction products. The average values from this experiment (calculated as counts/second/second; c/s/s) are presented in TABLE 1 and show detection of all serotypes of *L. pneumophila* to concentrations as low as molecules of DNA per reaction.

TABLE 1

| L. pneumophila Serotype/ATCC No. | Molecules of L. pneumophila DNA | LCx ® rate (c/s/s) |
|---|---|---|
| 1/33153 | 100 | 4145.6 |
|  | 10 | 3880.2 |
| 2/33154 | 100 | 4284.7 |
|  | 10 | 3996.9 |
| 3/35251 | 100 | 4132.8 |
|  | 10 | 3431.9 |
| 4/33156 | 100 | 3852.4 |
|  | 10 | 3316.8 |
| 5/33216 | 100 | 3212.1 |

TABLE 1-continued

| L. pneumophila Serotype/ATCC No. | Molecules of L. pneumophila DNA | LCx ® rate (c/s/s) |
|---|---|---|
|  | 10 | 2448.8 |
| 6/33215 | 100 | 4188.7 |
|  | 10 | 3497.4 |
| 7/33823 | 100 | 4196.6 |
|  | 10 | 3805.5 |
| 8/35096 | 100 | 4370.8 |
|  | 10 | 3984.5 |
| 9/35289 | 100 | 4278.6 |
|  | 10 | 3951.4 |
| 10/43283 | 100 | 4283.0 |
|  | 10 | 4042.7 |
| 11/43130 | 100 | 4483.1 |
|  | 10 | 3970.3 |
| 12/43290 | 100 | 4291.0 |
|  | 10 | 4056.7 |
| 13/43736 | 100 | 4264.1 |
|  | 10 | 3645.1 |
| 14/43703 | 100 | 4145.8 |
|  | 10 | 4015.7 |
| Negative Control |  | 90.1 |

Example 3

Specificity of *L. pneumophila* Detection

Purified DNA from 21 non-pneumophila members of the genus Legionella was purchased from BRL, Rockville, Md. The Legionella species obtained were: *L. anisa* (ATCC No. 35292), *L. brunensis* (ATCC No. 43878), *L. cherri* (ATCC No. 35252), *L. gormanii* (ATCC No. 43769), *L. gratiana* (ATCC No. 49413), *L. hackeliae* (ATCC No. 35250), *L. israeliensis* (ATCC No. 43119), *L. jamestowniensis* (ATCC No. 35298), *L. Iongbeachae* (ATCC No. 33462), *L. maceachernii* (ATCC No. 35300), *L. micdadei* (ATCC No. 33204), *L. moravica* (ATCC No. 43877), *L. oakridgensis* (ATCC No. 33761), *L. parisensis* (ATCC No. 35299), *L. rubrilucens* (ATCC No. 35304), *L. sainthelensi* (ATCC No. 49322), *L. santicrucis* (ATCC No. 35301), *L. spiritensis* (ATCC No. 35249), *L. steigerwaltii* (ATCC No. 35302), *L. tucsonensis* (ATCC No. 49180) and *L. wadsworthii* (ATCC No. 33877).

An additional 9 members of the genus Legionella, *L. birminghamensis* (ATCC No. 43702), *L. bozemanni* (ATCC No. 33217), *L. cincinnatiensis* (ATCC No. 43753), *L. dumoffi* (ATCC No. 35850), *L. erythra* (ATCC No. 35303), *L. fairfieldensis* (ATCC No. 49588), *L. feeleii* serogroup 2 (ATCC No. 35849), *L. jordanis* (ATCC No. 33623) and *L. quinlivanii* (ATCC No. 43830) were obtained from the ATCC, Rockville, Md. and cultured in-house. DNA was extracted and purified from all cultured cells as in Example 2. Purified DNA from the 9 in-house cultures was quantitated by taking an absorbance reading at 260 nm using a spectrophotometer or by using Hoechst dye 33258 with Hoefer's DyNA Quant-200 fluorometer after running an aliquot on 0.7% agarose gel.

All DNA samples were diluted to $10^7$ molecules of DNA/reaction and assayed with $10^7$ molecules of purified *L. pneumophila* serotype 1 (ATCC No. 33153) DNA from Example 2 as a positive control and calf thymus DNA as a negative control. DNA samples were PCR amplified and detected using the primers (SEQ ID NOs. 2 and 3) and detection probe (SEQ ID NO. 4) described in Example 1 by the method described in Example 2 except that the reaction mixture contained 10 $\mu$g/ml calf thymus DNA instead of salmon sperm DNA, and used 2.5 mM $MgCl_2$. All samples were tested in duplicate.

The data from this experiment is presented in TABLE 2 and shows specific amplification and detection of *L. pneumophila* only, with no other Legionella species detected.

TABLE 2

| Legionella species | ATCC Number | LCx ® rate (c/s/s) |
|---|---|---|
| anisa | 35292 | 81.1 |
| birminghamensis | 43702 | 24.4 |
| bozemannii | 33217 | 39.8 |
| brunensis | 43878 | 342.7 |
| cherrii | 35252 | 89.9 |
| cincinnatiensis | 43753 | 32.5 |
| dumoffii | 35850 | 39.6 |
| erythra | 35303 | 24.2 |
| fairfieldensis | 49588 | 40.0 |
| feeleii subgrp. 2 | 35849 | 137.4 |
| gormanii | 43769 | 59.9 |
| gratiana | 49413 | 81.0 |
| hackeliae | 35250 | 71.1 |
| israelensis | 43119 | 86.5 |
| jamestowniensis | 35298 | 152.6 |
| jordanis | 33623 | 23.8 |
| longbeachae | 33462 | 352.5 |
| maceachernii | 35300 | 64.9 |
| micdadei | 33204 | 73.1 |
| moravica | 43877 | 107.9 |
| oakridgensis | 33761 | 75.7 |
| parisiensis | 35299 | 64.9 |
| quinlivanii | 43830 | 27.4 |
| rubrilucens | 35304 | 61.2 |
| sainthelensi | 49322 | 70.1 |
| santicrucis | 35301 | 247.3 |
| spiritensis | 35249 | 224.1 |
| steigerwaltii | 35302 | 371.4 |
| tucsonensis | 49180 | 340.5 |
| wadsworthii | 33877 | 145.0 |
| Positive Control (*pneumophila*) | 33153 | 4367.7 |
| Negative Control |  | 319.2 |

Example 4

Comparison of *L. pneumophila* Detection by OH-PCR and Culture

Forty sputum samples were obtained from patients with atypical pneumonia, suspected of having Legionellosis, from Biotech Research Labs, Rockville, Md. and were tested for *L. pneumophila* by traditional culture methodology at BRL and compared to L. pneumophila detection using primers (SEQ ID NO 2 and SEQ ID NO 3) and detection probe (SEQ ID NO 4) as described in Example 1. Samples were liquefied with 333 mM Dithiothreitol at pH 4.1 for 10 minutes then centrifuged at 3000×g for 15 minutes, washed with 20 mM Tris, pH 8.3, and resuspended in 20 mM Tris, pH 8.3 containing 1 mM EDTA. Samples were then lysed with 60% (w/v) Chelax-100 at 95° C. for 30 minutes and centrifuged at 10,000×g for 2 minutes. Thirty microliters of the sample were added to 60 μl of sterilized water and 10 μl of $MgCl_2$ at a final concentration of 5.0 mM of sample mixture. The sample mixture was then amplified using an equal volume of Taq polymerase at a concentration of 2 units/reaction, nucleotides at 400 nM each, primers at a concentration of 400 nM each, 20 nM of detection probe, all contained in 80 mM Tris, pH 8.3, 0.1 mM EDTA, 0.01% Nipaset, 0.1% Tween 20, 0.0005% Quinolone and PCR buffer II (Perkin Elmer, Foster City, Calif.) containing 20 mM Tris-HCl, pH 8.3 and 100 mM KCl, for a total reaction volume of 0.2 ml. Samples were tested in single replicates with calf thymus DNA as the negative control and 25 molecules of purified *L. pneumophila* serotype 1 (ATCC No. 33153) DNA as the positive control; the same experiment was repeated ten days later. Cycling conditions and product detection was the same as in Example 2. Results are shown in TABLE 3.

TABLE 3

| | | LCx ® rate (c/s/s) | |
|---|---|---|---|
| Sample No. | Culture Result | Experiment 1 | Experiment 2 |
| 1 | nd | 39.5 | 55.4 |
| 2 | NEGATIVE | 49.4 | 112.8 |
| 3 | nd | 98.9 | 62.6 |
| 4 | POSITIVE | 2603.9 | 2797.6 |
| 5 | NEGATIVE | 21.3 | 69.2 |
| 6 | NEGATIVE | 50.3 | 120.9 |
| 7 | nd | 17.7 | 18.3 |
| 8 | nd | 2424.8 | 2878.9 |
| 9 | nd | 35.3 | 82.0 |
| 10 | NEGATIVE | 37.4 | 42.2 |
| 11 | NEGATIVE | 18.3 | 50.7 |
| 12 | nd | 35.7 | 101.5 |
| 13 | nd | 21.9 | 20.1 |
| 14 | nd | 42.8 | 145.2 |
| 15 | NEGATIVE | 20.7 | 167.4 |
| 16 | NEGATIVE | 15.8 | 37.1 |
| 17 | NEGATIVE | 18.9 | 57.5 |
| 18 | NEGATIVE | 2764.5 | 248.8 |
| 19 | nd | 72.1 | 109.6 |
| 20 | NEGATIVE | 87.5 | 141.2 |
| 21 | NEGATIVE | 54.9 | 157.7 |
| 22 | nd | 74.5 | 207.3 |
| 23 | nd | 70.3 | 232.5 |
| 24 | nd | 47.7 | 207.6 |
| 25 | nd | 58.5 | 305.6 |
| 26 | nd | 71.5 | 210.7 |
| 27 | NEGATIVE | 45.4 | 136.1 |
| 28 | nd | 43.4 | 89.2 |
| 29 | NEGATIVE | 103.7 | 268.7 |
| 30 | NEGATIVE | 26.5 | 56.1 |
| 31 | nd | 16.3 | 35.0 |
| 32 | NEGATIVE | 122.5 | 303.2 |
| 33 | nd | 75.2 | 326.9 |
| 34 | nd | 38.4 | 95.2 |
| 35 | nd | 83.5 | 114.9 |
| 36 | POSITIVE | 2566.5 | 1939.2 |
| 37 | POSITIVE | 2615.6 | 2243.8 |
| 38 | NEGATIVE | 111.3 | 179.8 |
| 39 | NEGATIVE | 42.9 | 136.3 |
| 40 | NEGATIVE | 19.1 | 58.9 |
| Neg. Control mean | | 23.7 | 47.0 |
| Pos. Control mean | | 2802.6 | 2574.4 |

(nd = not determined)

The percentage of patients with atypical pneumonia that are found to have Legionellosis is 5 to 10%. Therefore one would expect 2 to 4 of the above samples to be positive for *L. pneumophila*. Three samples were found to be positive by culture, and all 3 were also positive for *L. pneumophila* in the LCx® assay. An LCx® reading of 500 or above was considered positive. One sample (#8) was also identified as positive for *L. pneumophila* by LCx® that was not tested positive by culture Additionally, sample #18, which was culture negative, was positive in initial LCx® testing, but gave a lower signal in repeat testing. Thus, the primers and probes herein provided proved to be at least as sensitive at detecting *L. pneumophila* as traditional culture methods.

While the invention has been described in detail and with reference to specific embodiments, it will be apparent to one skilled in embodiments without various changes and modifications may be made to such embodiments without departing from the spirit and scope of the invention.

What is claimed is:

1. A method of detecting the presence of *L. pneumophila* in a test sample comprising the steps of:

a) forming a reaction mixture comprising nucleic acid amplification reagents, a test sample containing a *L. pneumophila* target sequence, a primer pair (SEQ ID NOs. 2 and 3 or homologs of SEQ ID NOs. 2 and 3) and a probe (and SEQ ID NO. 4 or homologs of SEQ ID NO. 4);

b) subjecting said mixture to hybridization and extension conditions to generate at least one nucleic acid sequence complementary to said target sequence;

c) hybridizing said probe to said nucleic acid complementary to said target sequence so as to form a hybrid comprising said probe and said nucleic acid; and d) detecting said hybrid as an indication of the presence of *L. pneumophila* in said sample.

2. The method of claim 1 wherein said probe is labeled.

3. The method of claim 1 wherein said probe is labeled with a capture label and said primer is labeled with a detection label.

4. The method of claim 1 wherein said probe is labeled with a detection label and said primer is labeled with a capture label.

5. A kit comprising:

(a) SEQ ID NOs. 2, 3 and 4, or homologs of SEQ ID NOs. 2, 3 and 4; and (b) amplification reagents.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
       (A) LENGTH: 200 base pairs
       (B) TYPE: nucleic acid
       (C) STRANDEDNESS: double
       (D) TOPOLOGY: linear (ii) MOLECULE TYPE: genomic DNA (L. pneumophila)

(xi) SEQUENCE DESCRIPTION: SEQ ID NO:1:

```
TGGCTCTCAA TTGGCTTTAA CCGAACAGCA AATGAAAGAC GTTCTTAACA        50

AGTTTCAGAA AGATTTGATG GCTAAGCGTA CTGCTGAATT CAATAAGAAA       100

GCGGATGAAA ATAAAGTAAA AGGGGAAGCC TTTTTAACTG AAAACAAAAA       150

CAAGCCAGGC GTTGTTGTAT T

-continued

```
        (D) TOPOLOGY: linear (ii) MOLECULE TYPE: synthetic DNA (xi) SEQUENCE DESCRIPTION: SEQ ID NO:5:

GTCTTTCATT TGCTGTTCGG                                              20

(2) INFORMATION FOR SEQ ID NO:6:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: synthetic DNA (xi) SEQUENCE DESCRIPTION: SEQ ID NO:6:

GTTGTATTGC CAAGTGGTTT G                                            21

(2) INFORMATION FOR SEQ ID NO:7:

(i) SEQUENCE CHARACTERISTICS:
          (A) LENGTH: 15 base pairs
          (B) TYPE: nucleic acid
          (C) STRANDEDNESS: single
          (D) TOPOLOGY: linear (ii) MOLECULE TYPE: synthetic DNA (xi) SEQUENCE DESCRIPTION: SEQ ID NO:7:

ATTTTCATCC GCTTT                                                   15
```